(12) United States Patent
Isbell et al.

(10) Patent No.: US 6,201,144 B1
(45) Date of Patent: *Mar. 13, 2001

(54) PREPARATION OF SECONDARY ETHER FATTY ACIDS AND ESTERS FROM THEIR HYDROXY FATTY ACID EQUIVALENTS

(75) Inventors: Terry A. Isbell, Elmwood; Melissa S. Mund, Washington, both of IL (US)

(73) Assignee: The United States of America as represented by the Secretary of Agriculture, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/654,654

(22) Filed: May 29, 1996

(51) Int. Cl.[7] .................................................. C07C 59/00
(52) U.S. Cl. .......................... 554/213; 554/149; 554/156; 554/218; 508/501
(58) Field of Search .................................... 554/213, 218, 554/149, 156, 169; 508/501

(56) References Cited

U.S. PATENT DOCUMENTS

| | | | |
|---|---|---|---|
| 1,863,004 | * | 6/1932 | Burwell ................................ 508/312 |
| 2,542,062 | * | 2/1951 | Severn . |
| 3,035,069 | * | 5/1962 | Findley et al. . |
| 3,732,264 | * | 5/1973 | Baum et al. . |
| 3,873,586 | * | 3/1975 | Henrick . |
| 4,364,743 | * | 12/1982 | Erner . |
| 4,366,151 | * | 12/1982 | Oppenlaender et al. . |
| 5,164,124 | * | 11/1992 | Lange et al. . |
| 5,294,731 | * | 3/1994 | Paust et al. ........................... 554/213 |

OTHER PUBLICATIONS

RN 61523–42–0 CA. Month Unavailable 1993.*
RN 150017–71–3 CA. Month Unavailable 1993.*
RN 86838–53–1 CA. Month Unavailable 1983.*
RN 149755–17–9 CA. Date Unavailable.*

* cited by examiner

*Primary Examiner*—Margaret Medley
(74) *Attorney, Agent, or Firm*—M. Howard Silverstein; Joseph A. Lipovsky; John D. Fado

(57) ABSTRACT

Fatty ether compounds and a process for their production is disclosed. The compounds possess low viscosity and low temperature melting point properties and may be used as viscosity modifiers in the creation of cosmetics and complete vegetable oil based biodegradable fluids such as hydraulic fluids and dielectric fluids. Formation of these fatty ether compounds is by reaction of the appropriate hydroxy fatty acid or lactone with a nucleophilic alcohol in the presence of an acid catalyst to produce fatty ether esters. Following their formation, the fatty ether esters may be recovered for subsequent use, or in the alternative, they may either be hydrolyzed to produce fatty ether acids or transesterified with a different nucleophilic alcohol in the presence of an acid catalyst to produce alternate ester variants.

11 Claims, No Drawings

PREPARATION OF SECONDARY ETHER FATTY ACIDS AND ESTERS FROM THEIR HYDROXY FATTY ACID EQUIVALENTS

BACKGROUND OF THE INVENTION

1. Field of the Invention

This invention relates to a novel process for the production of previously unknown secondary ether fatty acids and secondary ether esters from either their equivalent fatty acids possessing an alcohol in the 4,5 or 6 position or, in the alternative, from their equivalent lactone precursors.

2. Description of the Prior Art

Production of hydroxy fatty acids and lactones utilizable as the starting material for the methods and products of the instant invention has been previously taught in the art.

U.S. patent application 08/534,810 filed Sep. 27, 1995, entitled "Method for Development of δ-Lactones and Hydroxy Acids form Unsaturated Fatty Acids and Their Glycerides", and herein incorporated by reference, teaches the formation of δ-lactones and 5-hydroxy fatty acids.

U.S. Pat. No. 5,380,894 to Burg et al. teaches the formation of 5-,6- and 7-hydroxy fatty acids from the hydrolysis of estolides which were in turn produced from the reaction of one or a mixture of unsaturated fatty acids in the presence of a catalyst at elevated temperature and pressure.

Showell et al. (1968, J. Org. Chem., 33:2697–2704) disclose the production of γ-lactones from oleic acid, undecylenic acid and erucic acid by perchloric acid isomerization. Hydrolysis of these γ-lactones is subsequently carried out to yield 4-hydroxy fatty acids.

High yields of δ-lactones have been achieved by the acid catalyzed reaction of a 4-hexenoic acid containing a carbocation stabilizing functionality as described by Fujita et al. (1982, J. Chem. Tech. Biotechnol., 32:476–484).

Ballantine et al. ("Organic Reactions Catalysed by Sheet Silicates: Ether Formation by the Intermolecular Dehydration of Alcohols and by the Addition of Alcohols to Alkenes"; J. Mol. Catal., 1984, 26, 37–56) teach that primary alcohols may be converted to ethers through the use of ion-exchanged montmorillonites as heterogenous catalysts in pressure vessels at 200° C. Secondary alcohols, in the presence of acid catalysts, typically undergo dehydration to their corresponding stable alkenes. As shown in Table 2 of Ballantine's article, ether yields from secondary alcohols in this reaction never exceeded 35% and were, except for a singular occurrence, below 10%.

SUMMARY OF THE INVENTION

We have now invented a process for the production of novel fatty ether esters and fatty ether acids, which possess low viscosity and low temperature melting point properties and may be used as viscosity modifiers in the creation of cosmetics and complete vegetable oil based biodegradable fluids such as hydraulic fluids and dielectric fluids. The fatty ethers are of the formula(I):

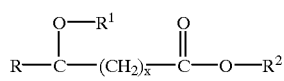

(I)

wherein R is selected from $C_7$–$C_{17}$ aliphatic hydrocarbons which may be saturated or unsaturated, linear or branched, and may be optionally substituted, such as with one or more hydroxy groups; $R^1$ is selected from linear or branched $C_1$–$C_{24}$ hydrocarbons which may be saturated or unsaturated, linear or branched, aliphatic or aromatic, and may be optionally substituted by one or more hydroxyl, halo, or amine groups; with the proviso that when $R^1$ is aromatic, it is limited to an optionally substituted six member carbon ring; and $R^2$ is selected from hydrogen or from linear or branched $C_1$–$C_{24}$ hydrocarbons which may be saturated or unsaturated, linear or branched, aliphatic or aromatic, and may be optionally substituted by one or more hydroxyl, halo, or amine groups; with the proviso that when $R^2$ is aromatic, it is limited to an optionally substituted six member carbon ring; and x is an integer from 2 to 4.

Formation of these fatty ether compounds is by reaction of the appropriate hydroxy fatty acid or lactone with a nucleophilic alcohol in the presence of an acid catalyst to produce fatty ether esters. Following their formation, the fatty ether esters may be recovered for subsequent use, or in the alternative, they may either be hydrolyzed to produce fatty ether acids or transesterified with a different nucleophilic alcohol in the presence of an acid catalyst to produce alternate ester variants.

In accordance with this discovery, it is an object of the invention to provide novel fatty ether compounds having utility as viscosity modifiers, hydraulic fluids and dielectric fluids.

It is a further object of the invention to provide a method of making these fatty ether compounds.

Other objects and advantages of the invention will become readily apparent from the ensuing description.

DETAILED DESCRIPTION OF THE INVENTION

Starting materials for use in the instant invention include one or a mixture of 4,5 or 6 hydroxy fatty acids of the formula (II):

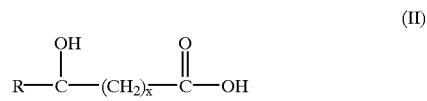

(II)

wherein R is selected from $C_7$–$C_{17}$ hydrocarbons which may be saturated or unsaturated, linear or branched, and may contain other substituents, such as one or more hydroxy groups; and x is an integer from 2 to 4; or one or more of a mixture of γ-, δ- or ε-lactones of the formula (III):

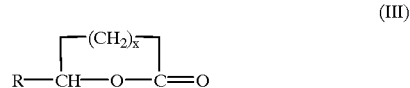

(III)

wherein R is selected from $C_7$–$C_{17}$ hydrocarbons which may be saturated or unsaturated, linear or branched, and may contain other substituents, such as one or more hydroxy groups, and x is an integer from 2 to 4;

The hydroxy fatty acids and lactones of formulas (II) and (III) may be acquired from natural sources or synthesized by means readily known to those of skill in the art. Useable fatty acid source materials, which may be converted by art-disclosed means into the hydroxy fatty acid and lactone starting materials of formulas (II) and (III), include the $\Delta^5$ and $\Delta^6$ unsaturated fatty acids in either the free or glyceryl ester form. These occur naturally in a variety of plant oils and may be conveniently obtained for use therefrom. Meadowfoam oil, having a high content of $\Delta^5$ unsaturated fatty acids is particularly preferred as a source material for preparation of the starting materials of the instant invention. Without being limited thereto, other oils such as pine oils, marsh-marigold oils, or oils of the carrot family (i.e. coriander, dill and fennel) may be used as sources.

Any monounsaturated vegetable oil including soybean oil, rapeseed oil, canola oil, sunflower oil, peanut oil and cottonseed oil may also be converted into its corresponding γ-lactone by means of an acid catalyzed isomerization at 100° C. and thus also be used as a source material for preparation of the starting materials of the instant invention.

As starting materials in the reaction of the invention, the hydroxy fatty acids and/or lactones may be provided in substantially pure form or, in the alternative, as a mixture and/or in an impure form.

The novel fatty ether esters of the invention are prepared by a reaction of one or more of the fatty acids of formula (II)

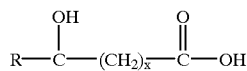

(II)

wherein R is selected from $C_7$–$C_{17}$ hydrocarbons which may be saturated or unsaturated, linear or branched, and may contain other substituents, such as one or more hydroxy groups; and x is an integer from 2 to 4; and/or one or more of a mixture of γ-, δ- or ε-lactones of formula (III):

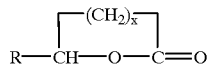

(III)

wherein R is selected from $C_7$–$C_{17}$ hydrocarbons which may be saturated or unsaturated, linear or branched, and may contain other substituents, such as one or more hydroxy groups, and x is an integer from 2 to 4; with a primary or secondary alcohol in the presence of a suitable acid catalyst under suitable conditions of temperature, pressure, reactant ratios and time to form fatty ether esters of formula (IV):

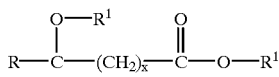

(IV)

wherein R is selected from $C_7$–$C_{17}$ hydrocarbons which may be saturated or unsaturated, linear or branched, and may contain other substituents, such as one or more hydroxy groups; each $R^1$ is identical and is selected from linear or branched $C_1$–$C_{24}$ hydrocarbons which may be saturated or unsaturated, linear or branched, aliphatic or aromatic, and may be optionally substituted by one or more hydroxy, halo, aromatic or amine groups; with the proviso that when $R^1$ is aromatic, it is limited to an optionally substituted six member carbon ring; and x is an integer from 2 to 4.

Preferred fatty ether esters include those formed by reaction of 4- and 5-hydroxy fatty acids with either straight or branched primary and secondary alcohols possessing 1 to 24 carbon atoms. These compounds are represented by the structure of formula (IV) wherein R, $R^1$, and x are as described above except that x is an integer from 2 to 3.

Particularly preferred fatty ether esters include those formed by reaction of 5-hydroxy fatty acids with primary and secondary alcohols possessing 1 to 24 carbon atoms. These compounds are represented by the structure of formula (IV) wherein R, $R^1$, and x are as described above except that x is the integer 3.

Conditions for the formation of the fatty ether esters of formula (IV) include reaction temperatures ranging from about 25° C. to about 200° C., preferably from about 80° C. to about 140° C. While the reaction is envisioned as being performed at ambient pressure, this is primarily due to simplicity of operation—with either higher or lower pressures being useable so long as such do not interfere with the reaction (e.g. excessively low pressures would cause a boiling off of one or more reactants). Reactant ratios of nucleophilic alcohol to hydroxy fatty acid and/or lactone range from about 2 to about 40 mole equivalents, with a range of about 10 to about 20 mole equivalents being preferred. Suitable acid catalysts include mineral acids such as perchloric acid and sulfuric acid; Lewis acids such as boron triflouride, tin octoate and zinc chloride; and heterogenous catalysts such as clays and ion-exchange resins. The acid catalysts are present in an amount ranging from about 0.01 to about 6.4 mole equivalents of the hydroxy fatty acid and/or lactone. The nucleophilic alcohols are straight chain or branched and can be primary or secondary in nature. Reaction times are envisioned to run from about 1 to about 100 hours, with a range of about 2 to about 24 hours being preferred. Production of the fatty ether esters by this reaction range from about 70% to about 90% of the theoretical yield; their separation from the reaction mixture may be accomplished by any art-known means such as vacuum distillation under reduced pressure.

The ether fatty esters of formula (IV) thus produced may in turn be hydrolyzed by reaction with a base to produce the ether fatty acids of formula (V):

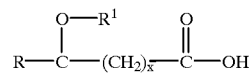

(V)

wherein R is selected from $C_7$–$C_{17}$ hydrocarbons which may be saturated or unsaturated, linear or branched, and may contain other substituents, such as one or more hydroxy groups; $R^1$ is selected from linear or branched $C_1$–$C_{24}$ hydrocarbons which may be saturated or unsaturated, linear or branched, aliphatic or aromatic, and may be optionally substituted by one or more hydroxy, halo, aromatic or amine groups; with the proviso that when $R^1$ is aromatic, it is limited to an optionally substituted six member carbon ring; and x is an integer from 2 to 4. This is accomplished by treatment of the ether fatty ester with an alcoholic mixture containing from about 0.1 to about 2.0 M of an alkaline earth or alkaline metal hydroxide such as potassium, sodium, calcium or lithium hydroxide. Reactions were run under the alcohol's reflux temperature, preferably at temperatures ranging from about 60° C. to about 120° C. for 1 hour and then cooled to room temperature and neutralized with dilute mineral acid to a pH of about 5.5. The water layer is then separated from the organic phase and residual solvents are removed under vacuum to afford the ether. One would also expect this hydrolysis to occur with high pressure steam splitting, as currently used in industrial settings.

In the alternative, the ether fatty esters of formula (IV) may be transesterified with a second nucleophilic alcohol in the presence of an acid catalyst using the same protocol as the previously described esterification reaction with the exception that temperatures ranging from about 25° C. to about 120° C., preferably from about 60° C. to about 110° C. are used, and that reactant ratios of from about 0.01 to about 0.1 mole equivalents of acid and from about 1 to about 10 mole equivalents of alcohol per mole equivalent of fatty ester are utilized. The resultant products are ether fatty esters of formula (VI):

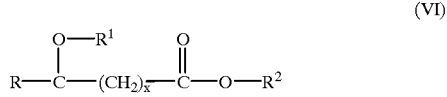

(VI)

wherein R is selected from $C_7$–$C_{17}$ hydrocarbons which may be saturated or unsaturated, linear or branched, and may contain other substituents, such as one or more hydroxy groups; each of $R^1$ and $R^2$ are independently selected from linear or branched $C_1$–$C_{24}$ hydrocarbons which may be saturated or unsaturated, linear or branched, aliphatic or aromatic, and may be optionally substituted by one or more hydroxy, halo, aromatic or amine groups; with the proviso that when either $R^1$ or $R^2$ is aromatic, it is limited to an optionally substituted six member carbon ring; and x is an integer from 2 to 4.

The following examples are intended to further illustrate the invention and are not intended to limit the scope of the invention which is defined by the claims.

EXAMPLE 1

A series of reactions were conducted to examine the production of 5-alkoxy eicosanoates from δ-lactones obtained from meadowfoam oil by the process described in U.S. patent application Ser. No. 08/534,810, filed Sep. 27, 1995, entitled "Method for Development of δ-Lactones and Hydroxy Acids from Unsaturated Fatty Acids and Their Glycerides", and herein incorporated by reference. δ-lactone was dissolved in the appropriate alcohol and reacted under the conditions listed in Table 1. Mixing was maintained throughout the course of the reaction by magnetic stirring or overhead stirring in larger scale reactions. The reaction vessels were fitted with reflux condensers to recycle volatile alcohols back into the reaction mixture. Temperature was maintained in the reaction via a temperature controller with a thermocouple immersed in the reaction mixture, except those reactions that were conducted at the alcohol's boiling point. Isolation and workup of the reaction are listed below based on the catalyst employed.

$BF_3$ workup:

After the reaction reached completion, the crude reaction mixture was poured into a separatory funnel and diluted with 50 mL hexane, washed 2×10 mL with saturated NaCl solution, dried over $Na_2SO_4$, gravity filtered through a #1 Whatman filter paper and concentrated in vacuo. Kugelrohr distillation at 160° C.–180° C. (0.2 mm Hg) to remove unsaturated byproducts and excess alcohol provided isolated ethers.

Clay workup:

After the reaction reached completion, the crude reaction mixture was diluted in 50 mL of hexane, filtered through #1 Whatman filter paper using a buchner funnel and vacuum filtration flask and concentrated in vacuo. Kugelrohr distillation at 160° C.–180° C. (0.2 mm Hg) to remove unsaturated byproducts and excess alcohol, provided the isolated ethers.

$HClO_4$ workup:

After the reaction reached completion, the crude reaction mixture was poured into a separatory funnel and diluted with 50 mL of hexane, washed 2×10 mL with 0.5M $Na_2HPO_4$ solution, dried over $Na_2SO_4$, gravity filtered through a #1 Whatman filter paper and concentrated in vacuo. Kugelrohr distillation at 160° C.–180° C. (0.2 mm Hg) to remove unsaturated byproducts and excess alcohol provided the isolated ethers.

$H_2SO_4$ workup:

After the reaction reached completion, the crude reaction mixture was poured into a separatory funnel and diluted with 50 mL of hexane, washed 2×10 mL with 0.5M $Na_2HPO_4$ solution, dried over $Na_2SO_4$, gravity filtered through a #1 Whatman filter paper and concentrated in vacuo. Kugelrohr distillation at 160° C.–180° C. (0.2 mm Hg) to remove unsaturated byproducts and excess alcohol provided the isolated ethers.

EXAMPLE 2

A series of reactions were conducted the same as in Example 1, except substituting γ-lactone for δ-lactone. γ-lactone was dissolved in the appropriate alcohol and reacted under the conditions listed in Table 2. Workup and isolation of the ether is the same as described above in Example 1, being dependent on the catalyst used.

EXAMPLE 3

A series of reactions conducted in the same manner as that of Example 1, except substituting 5-hydroxy eicosanoic acid for δ-lactone. The 5-hydroxy eicosanoic acid was dissolved in the appropriate alcohol and reacted under the conditions listed in Table 3. Workup and isolation of the ether is the same as described above in Example 1, being dependent on the catalyst used.

TABLE 1

| Substrate | Catalyst | Catalyst Equivalents* | Alcohol | Alcohol Volume | Temp. (° C.) | Reaction Time (h) | Percent Ether | Percent Unsaturated |
| --- | --- | --- | --- | --- | --- | --- | --- | --- |
| δ-Lactone | $BF_3$ | 6.4 | Methanol | 5 mL | 67 | 24 | 86 | 10 |
| δ-Lactone | $BF_3$ | 4.5 | Butanol | 5 mL | 85 | 19 | 84 | 13 |
| δ-Lactone | $BF_3$ | 4.5 | Decanol | 5 mL | 85 | 24 | 93 | 7 |
| δ-Lactone | $BF_3$ | 1.0 | 2-Ethylhexanol | 10 mL | 120 | 1.5 | 57 | 36 |
| δ-Lactone | Clay | 0.1 g | Methanol | 5 mL | 67 | 24 | 0.1 | 19 |
| δ-Lactone | Clay | 0.1 g | Butanol | 5 mL | 117 | 21 | 70 | 17 |
| δ-Lactone | Clay | 0.1 g | Decanol | 5 mL | 115 | 24 | 82 | 12 |
| δ-Lactone | Clay | 0.1 g | 2-Ethylhexanol | 5 mL | 120 | 22 | 84 | 11 |

*Equivalents = mole of substrate per mole of catalyst except for clay which is reported as mass of clay.

TABLE 2

| Substrate | Catalyst | Catalyst Equivalents* | Alcohol | Alcohol Volume | Temp. (° C.) | Reaction Time (h) | Percent Ether | Percent Unsaturated |
|---|---|---|---|---|---|---|---|---|
| γ-Lactone | BF$_3$ | 4.5 | Methanol | 5 mL | 67 | 142 | 44 | 3 |
| γ-Lactone | BF$_3$ | 4.5 | Butanol | 5 mL | 85 | 94 | 76 | 8 |

*Equivalents = mole of substrate per mole of catalyst except for clay which is reported as mass of clay.

TABLE 3

| Substrate | Catalyst | Catalyst Equivalents* | Alcohol | Alcohol Volume | Temp. (° C.) | Reaction Time (h) | Percent Ether | Percent Unsaturated |
|---|---|---|---|---|---|---|---|---|
| 5-Hydroxyeicosanoic acid | BF$_3$ | 4.5 | Butanol | 5 mL | 85 | 22 | 83 | 14 |
| 5-Hydroxyeicosanoic acid | BF$_3$ | 1.0 | 2-Ethylhexanol | 25 mL | 120 | 18 | 80 | 14 |
| 5-Hydroxyeicosanoic acid | Clay | 2.0 g | Butanol | 10 mL | 98 | 35 | 30 | 12 |
| 5-Hydroxyeicosanoic acid | HClO$_4$ | 0.4 | Methanol | 10 mL | 67 | 25 | 4 | 5 |
| 5-Hydroxyeicosanoic acid | HClO$_4$ | 0.5 | Butanol | 10 mL | 110 | 18 | 74 | 21 |
| 5-Hydroxyeicosanoic acid | HClO$_4$ | 0.5 | Decanol | 10 mL | 100 | 2 | 69 | 8 |
| 5-Hydroxyeicosanoic acid | HClO$_4$ | 0.3 | 2-Ethylhexanol | 5 mL | 90 | 19 | 84 | 16 |
| 5-Hydroxyeicosanoic acid | H$_2$SO$_4$ | 2.0 | Butanol | 10 mL | 110 | 18 | 67 | 33 |

*Equivalents = mole of substrate per mole of catalyst except for clay which is reported as mass of clay.

We claim:

1. Fatty ether esters of the formula (IV):

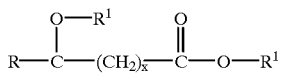

(IV)

wherein R is selected from C$_7$–C$_{17}$ aliphatic hydrocarbons which are saturated or unsaturated; both R$^1$ substituents are identical and are selected from the group consisting of ethyl, isopropyl, n-butyl, 2-ethylhexyl and decyl; and x is 3.

2. Fatty ether esters of the formula (IV):

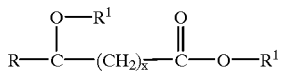

(IV)

wherein R is selected from C$_7$–C$_{17}$ aliphatic hydrocarbons which are saturated or unsaturated; R$^1$ represents 2-heptyl undecyl; and x is 3.

3. Fatty ether esters of the formula (IV):

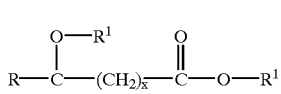

(IV)

wherein R is selected from C$_7$–C$_{17}$ aliphatic hydrocarbons which are saturated or unsaturated; R$^1$ represents stearyl; and x is 3.

4. Fatty ether esters of the formula (IV):

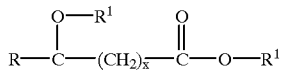

(IV)

wherein R is selected from C$_7$–C$_{17}$ aliphatic hydrocarbons which are saturated or unsaturated; R$^1$ represents oleyl; and x is 3.

5. A method of making the fatty ether esters of the formula (I):

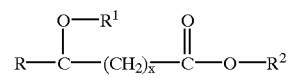

(I)

wherein R is selected from C$_7$–C$_{17}$ aliphatic hydrocarbons which are saturated or unsaturated; R$^1$ is linear or branched C$_1$–C$_{24}$ hydrocarbons which may be saturated or unsaturated with the proviso that when R$^1$ is aromatic, it is limited to an optionally substituted six member carbon ring; and R$^2$ is selected from or from linear or branched C$_1$–C$_{24}$ aliphatic hydrocarbons; and x is an integer from 2 to 4;

comprising the steps of:

a. reacting of one or more of the fatty acids of formula (II):

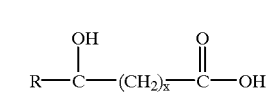

(II)

wherein R is selected from C$_7$–C$_{17}$ aliphatic hydrocarbons which are saturated or unsaturated; and x is an integer from 2 to 4; and/or one or more of a mixture of γ-, δ- or ε-lactones of formula (III):

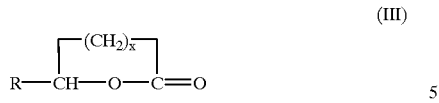

(III)

wherein R is selected from $C_7$–$C_{17}$ aliphatic hydrocarbons which are saturated or unsaturated; and x is an integer from 2 to 4; with a primary or secondary alcohol possessing 1 to 24 carbons in the presence of an acid catalyst wherein said reaction is carried out for about 2 to about 24 hours at a temperature ranging from about 65° C. to about 130° C. and wherein the molar ratio of said alcohol to said hydroxy fatty acid or lactone ranges from about 2:1 to about 40:1 for the production of fatty ether esters; and b. separating said fatty ether ester from the reaction mixture.

6. The method of claim 5 wherein said reaction is carried out for about 2 to about 24 hours at a temperature ranging from about 80° C. to about 130° C.

7. The method of claim 5 wherein the molar ratio of said alcohol to said hydroxy fatty acid and/or lactone ranges from about 10:1 to about 20:1.

8. The method of claim 5 wherein said acid catalyst is selected from the group consisting of mineral acids, Lewis acids and heterogenous catalysts and is present in the reaction mixture at a molar ratio of said catalyst to said hydroxy fatty acid and/or lactone ranging from about 0.01:1 to about 8:1.

9. The method of claim 5 wherein the yield of fatty ether ester ranges from about 65% to about 90%.

10. The method of making fatty ether acids comprising the steps of :

a. reacting of one or more of the fatty acids of formula (II):

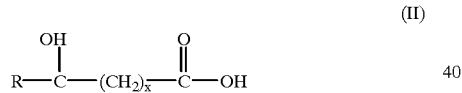

(II)

wherein R is selected from $C_7$–$C_{17}$ aliphatic hydrocarbons which are saturated or unsaturated; and x is an integer from 2 to 4; and/or one or more of a mixture of γ-, δ- or ε-lactones of formula (III):

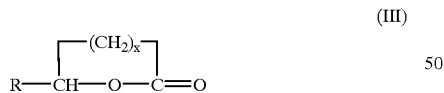

(III)

wherein R is selected from $C_7$–$C_{17}$ aliphatic hydrocarbons which are saturated or unsaturated; and x is an integer from 2 to 4; with an aliphatic primary or secondary alcohol possessing 1 to 24 carbons in the presence of an acid catalyst wherein said reaction is carried out for about 2 to about 24 hours at a temperature ranging form about 65° C. to about 130° C. and wherein the molar ratio of said alcohol to said hydroxy fatty acid and or lactone ranges from about 2:1 to about 40:1 for the production of fatty ether esters;

b. separating said fatty ether ester from the reaction mixture; and c. subsequently reacting said fatty ether ester with a base to produce fatty ether acids of formula (V):

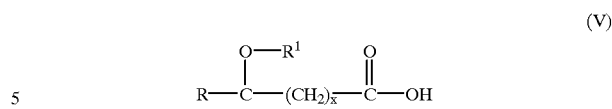

(V)

wherein R is selected from $C_7$–$C_{17}$ aliphatic hydrocarbons which are saturated or unsaturated, and linear or branched; $R^1$ is selected from linear or branched $C_1$–$C_{24}$ aliphatic hydrocarbons which are saturated or unsaturated, and linear or branched; and x is an integer from 2 to 4.

11. The method of making fatty ether esters comprising the steps of:

a. reacting of one or more of the fatty acids of formula (II):

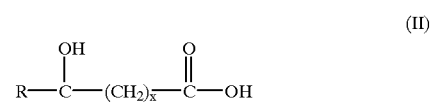

(II)

wherein R is selected from $C_7$–$C_{17}$ aliphatic hydrocarbons which are saturated or unsaturated; and x is an integer from 2 to 4; and/or one or more of a mixture of γ-, δ- or ε-lactones of formula (III):

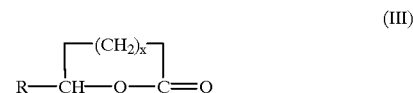

(III)

wherein R is selected from $C_7$–$C_{17}$ aliphatic hydrocarbons which are saturated or unsaturated; and x is an integer from 2 to 4; with a primary or secondary alcohol possessing 1 to 24 carbons in the presence of an acid catalyst wherein said reaction is carried out for about 2 to about 24 hours at a temperature ranging form about 65° C. to about 130° C. and wherein the molar ratio of said alcohol to said hydroxy fatty acid and or lactone ranges from about 2:1 to about 40;1 for the production of fatty ether esters, b. separating said fatty ether ester from the reaction mixture; and c. subsequently transesterifying said fatty ether ester with a second nucleophilic alcohol in the presence of an acid catalyst to produce the ether fatty esters of formula (VI):

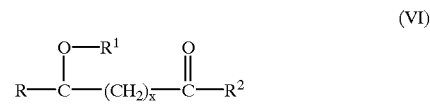

(VI)

wherein R is selected from $C_7$–$C_{17}$ aliphatic hydrocarbons which are saturated or unsaturated, and linear or branched; each of $R^1$ and $R^2$ are independently selected from linear or branched $C_1$–$C_{24}$ aliphatic hydrocarbons which are saturated or unsaturated, and linear or branched; and x is an integer from 2 to 4.

* * * * *